US00PP30919P3

(12) United States Plant Patent
Koot

(10) Patent No.: US PP30,919 P3
(45) Date of Patent: Oct. 1, 2019

(54) ***POINSETTIA* PLANT NAMED 'DUEPOJADOPIN'**

(50) Latin Name: *Euphorbia hybrida*
Varietal Denomination: Duepojadopin

(71) Applicant: DUMMEN GROUP B.V., De Lier (NL)

(72) Inventor: Arjan Koot, Oeffelt (NL)

(73) Assignee: Dümmen Group B.V., De Lier (NL)

( * ) Notice: Subject to any disclaimer, the term of this patent is extended or adjusted under 35 U.S.C. 154(b) by 0 days.

(21) Appl. No.: 15/732,736

(22) Filed: Dec. 21, 2017

(65) Prior Publication Data

US 2018/0184563 P1 Jun. 28, 2018

Related U.S. Application Data

(60) Provisional application No. 62/498,364, filed on Dec. 22, 2016.

(51) Int. Cl.
*A01H 5/02* (2018.01)
*A01H 6/38* (2018.01)

(52) U.S. Cl.
USPC ..... Plt./306
CPC ..... *A01H 5/02* (2013.01)

(58) Field of Classification Search
USPC ..... Plt./306
CPC ..... A01H 5/02; A01H 5/0244; A01H 6/38; A01H 6/385
See application file for complete search history.

(56) References Cited

PUBLICATIONS

Dole et al. New Poinsettias for 2018—How did they perform? Greenhouse Porduct News retrieved on Nov. 14, 2018 from the Internet at https://gpnmag.com/article/new-poinsettias-for-2018-how-did-they-perform/, pp. 1-7. (Year: 2018).*

Higgins. Reinventing the poinsettia, retrieved on Nov. 14, 2018 from the Internet at https://www.washingtonpost.com/lifestyle/home/reinventing-the-poinsettia-a-classic-christnnas-flowers-colorful-new-looks/2017/12/05/7eb7716c-d6bd-11e7-b62d-d9345ced896d_story.html?noredirect=on&utm_term=.4b165e154708, 1-4. (Year: 2018).*

Lucas Greenhouses 2017 Poinsettia Program, retrieved on Nov. 14, 2018 from the Internet at https://www.bfgsupply.com/_CE/pagecontent/Documents/Plant%20Connection/Lucas%20Poinsettia%20Product%20Listing%202017.pdf, 7 pp. (Year: 2017).*

* cited by examiner

*Primary Examiner* — June Hwu
(74) *Attorney, Agent, or Firm* — C. A. Whealy

(57) ABSTRACT

A new and distinct cultivar of *Poinsettia* plant named 'Duepojadopin', characterized by its upright to somewhat outwardly spreading and uniformly mounding plant habit; moderately vigorous growth habit; moderately strong lateral branches; relatively early flowering habit; inflorescences with pink-colored flower bracts; and excellent post-production longevity.

2 Drawing Sheets

Botanical designation: *Euphorbia hybrida.*
Cultivar denomination: 'DUEPOJADOPIN'.

BACKGROUND OF THE INVENTION

The present invention relates to a new and distinct cultivar of *Poinsettia* plant, botanically known as *Euphorbia hybrida*, and hereinafter referred to by the name 'Duepojadopin'.

The new *Poinsettia* plant is a product of a planned breeding program conducted by the Inventor in Rheinberg, Germany. The objective of the breeding program is to create moderately vigorous *Poinsettia* plants with strong lateral branches and attractive flower bract coloration.

The new *Poinsettia* plant originated from a cross-pollination made by the Inventor in July, 2012 in Rheinberg, Germany of a proprietary selection of *Euphorbia hybrida* identified as code number EE08-001047-002, not patented, as the female, or seed, parent with a proprietary selection of *Euphorbia hybrida* identified as code number EE-0386, not patented, as the male, or pollen, parent. The new *Poinsettia* plant was discovered and selected by the Inventor as a flowering plant from within the progeny of the stated cross-pollination in a controlled greenhouse environment in Rheinberg, Germany in December, 2016.

Asexual reproduction of the new *Poinsettia* plant by terminal vegetative cuttings in a controlled greenhouse environment in Rheinberg, Germany has shown that the unique features of this new *Poinsettia* plant are stable and reproduced true to type in successive generations of asexual reproduction.

SUMMARY OF THE INVENTION

Plants of the new *Poinsettia* have not been observed under all possible combinations of environmental conditions and cultural practices. The phenotype may vary somewhat with variations in environmental conditions such as temperature, daylength and light intensity, without, however, any variance in genotype.

The following traits have been repeatedly observed and are determined to be the unique characteristics of 'Duepojadopin'. These characteristics in combination distinguish 'Duepojadopin' as a new and distinct *Poinsettia* plant:

1. Upright to somewhat outwardly spreading and uniformly mounding plant habit.
2. Moderately vigorous growth habit.

3. Moderately strong lateral branches.
4. Relatively early flowering habit.
5. Inflorescences with pink-colored flower bracts.
6. Excellent post-production longevity.

Plants of the new *Poinsettia* differ primarily from plants of the female parent selection in the following characteristics:

1. Plants of the new *Poinsettia* flower earlier than plants of the female parent selection.
2. Plants of the new *Poinsettia* and the female parent selection differ in flower bract color as plants of the female parent selection have red-colored flower bracts.

Plants of the new *Poinsettia* differ primarily from plants of the male parent selection in the following characteristics:

1. Plants of the new *Poinsettia* are more freely branching than plants of the male parent selection.
2. Plants of the new *Poinsettia* and the male parent selection differ in flower bract color as plants of the male parent selection have white-colored flower bracts.

Plants of the new *Poinsettia* can be compared to plants of *Euphorbia pulcherrima* Willd. ex Klotzch X *Euphorbia cornastra* 'Bonpripicom', disclosed in U.S. Plant Pat. No. 21,325. In side-by-side comparisons, plants of the new *Poinsettia* differ primarily from plants of 'Bonpripicom' in the following characteristics:

1. Plants of the new *Poinsettia* are larger and more vigorous than plants of 'Bonpripicom'.
2. Plants of the new *Poinsettia* have longer internodes than plants of 'Bonpripicom'.
3. Plants of the new *Poinsettia* have narrower leaves than plants of 'Bonpripicom'.
4. Plants of the new *Poinsettia* have lighter-colored flower bracts than plants of 'Bonpripicom'.

BRIEF DESCRIPTION OF THE PHOTOGRAPHS

The accompanying photographs illustrate the overall appearance of the new *Poinsettia* plant showing the colors as true as it is reasonably possible to obtain in colored reproductions of this type. Colors in the photographs may differ slightly from the color values cited in the detailed botanical description which accurately describe the colors of the new *Poinsettia* plant.

The photographs on both sheets comprise side perspective views of typical flowering plants of 'Duepojadopin' grown in containers.

DETAILED BOTANICAL DESCRIPTION

The aforementioned photograph and following observations and measurements describe plants grown in Rheinberg, Germany during the summer and autumn in a glass-covered greenhouse and under cultural practices typical of commercial *Poinsettia* production. During the production of the plants, day and night temperatures averaged 18° C. and light levels averaged 4,500 lux. Single plants were grown in 12-cm containers and were pinched one time about three weeks after planting the cuttings. Plants were 16 weeks old when the photograph and the detailed description were taken. In the following description, color references are made to Pantone Color Chart, 2015 Edition, except where general terms of ordinary dictionary significance are used.

Botanical classification: *Euphorbia hybrida* 'Duepojadopin'.

Parentage:

*Female, or seed, parent*.—Proprietary selection of *Euphorbia hybrida* identified as code number EE08-001047-002, not patented.

*Male or pollen parent*.—Proprietary selection of *Euphorbia hybrida* identified as code number EE-0386, not patented.

Propagation:

*Type*.—Terminal vegetative cuttings.

*Time to initiate roots, summer*.—About five days at temperatures about 20° C.

*Time to initiate roots, winter*.—About seven days at temperatures about 20° C.

*Time to produce a rooted young plant, summer*.—About three weeks at temperatures about 20° C.

*Time to produce a rooted young plant, winter*.—About four weeks at temperatures about 20° C.

*Root description*.—Fine, fibrous; typically white in color, actual color of the roots is dependent on substrate composition, water quality, fertilizers, substrate temperature and age of roots.

*Rooting habit*.—Freely branching; dense.

Plant description:

*Plant habit and form*.—Upright to somewhat outwardly spreading and uniformly mounding plant habit; inverted triangle, mounding; inflorescences with large flower bracts positioned above the foliar plane; moderately vigorous growth habit.

*Plant height*.—About 22 cm.

*Plant diameter or spread*.—About 31.5 cm.

*Lateral branch description*.—Quantity: Freely branching habit with about four to five lateral branches developing after pinching. Length: About 17.3 cm. Diameter: About 6 mm. Internode length: About 1.3 cm. Strength: Moderately strong. Texture: Smooth, glabrous. Color: Close to 18-0130.

*Leaf description*.—Arrangement: Alternate, simple. Length: About 8.5 cm. Width: About 4 cm. Shape: Ovate. Apex: Apiculate. Base: Obtuse. Margin: Entire, with typically one or two shallow lobes. Texture, upper surface: Glabrous; smooth. Texture, lower surface: Glabrous; rugose. Venation pattern: Pinnate. Color: Developing leaves, upper surface: Close to 19-0230. Developing leaves, lower surface: Close to 18-0119. Fully expanded leaves, upper surface: Close to 19-0315; venation, close to 18-0328. Fully expanded leaves, lower surface: Close to 19-0230; venation, close to 17-0330. Petioles: Length: About 2.7 cm. Diameter: About 3 mm. Texture, upper and lower surfaces: Smooth, glabrous. Color, upper surface: Close to 19-1627. Color, lower surface: Close to 17-0330.

Inflorescence description:

*Inflorescence type and habit*.—Inflorescences are compound corymbs of cyathia with flower bracts subtending the cyathia; one inflorescence per lateral branch with inflorescences positioned above and beyond the foliar plane.

*Fragrance*.—None detected.

*Natural flowering season*.—Plants flower naturally during the autumn and winter under long nyctoperiod conditions; inflorescence initiation and development can be induced under artificial long nyctoperiod conditions; relatively early flowering habit, response time is about eight weeks.

*Post-production longevity*.—Excellent post-production longevity; plants of the new *Poinsettia* maintain good substance and bract color for about twelve weeks under interior conditions.

*Inflorescence size*.—Diameter: About 17 cm. Height (depth): About 4.1 cm.

*Flower bracts*.—Quantity per inflorescence: About 15. Length: About 8.5 cm. Width: About 4 cm. Shape: Ovate. Apex: Apiculate. Base: Obtuse. Margin: Entire, with typically one or two shallow lobes. Aspect: Mostly flat. Texture, upper surface: Glabrous; smooth. Texture, lower surface: Glabrous; rugose. Venation pattern: Pinnate. Color: Developing bracts, upper surface: Close to 17-2036. Developing bracts, lower surface: Close to 11-0809. Transitional and fully developed bracts, upper surface: Close to 17-2036; venation, close to 17-2036; color does not fade with development. Transitional and fully developed bracts, lower surface: Close to 11-0809; venation, close to 11-0809; color does not fade with development. Bract petioles: Length: About 1.3 cm. Diameter: About 2 mm. Texture, upper and lower surfaces: Smooth, glabrous. Color, upper and lower surfaces: Close to 16-0439.

*Cyathia*.—Quantity per corymb: About eleven. Length: About 8 mm. Width: About 6 mm. Shape: Ovoid. Texture, inner and outer surfaces: Smooth, glabrous. Color: When developing, inner surface: Close to 15-0341. When developing, outer surface: Close to 17-0336. Fully developed, inner and outer surfaces: Close to 17-0336. Nectaries: Quantity per cyathium: Typically one. Length: About 5 mm. Diameter: About 1 mm. Shape: Ovoid. Texture, inner and outer surfaces: Smooth, glabrous. Color: When developing and fully developed, inner surface: Close to 15-1062. When developing and fully developed, outer surface: Close to 13-0859.

*Peduncles*.—Length: About 4 mm. Diameter: About 1 mm. Strength: Strong. Texture: Smooth, glabrous. Color: Close to 15-0341.

*Reproductive organs*.—Stamens: Quantity per cyathium: About ten. Filament length: About 7 mm. Filament color: Close to 17-2120. Anther shape: Oval. Anther length: About 0.5 mm. Anther color: Close to 19-1627. Amount of pollen: Abundant. Pollen color: Close to 13-0858. Pistils: Quantity per cyathium: One. Pistil length: About 1 cm. Style length: About 2 mm. Style color: Close to 15-0341. Stigma shape: Crested. Stigma color: Close to 19-2024. Ovary color: Close to 17-0336. Seeds and fruits: Seed and fruit production have not been observed on plants of the new *Poinsettia* to date.

Disease & pest resistance: Plants of the new *Poinsettia* have not been shown to be resistant to pathogens and pests common to *Poinsettia* plants to date.

Temperature tolerance: Plants of the new *Poinsettia* have been observed to tolerate temperatures ranging from about 12° C. to about 40° C.

It is claimed:

1. A new and distinct *Poinsettia* plant named 'Duepojadopin' as illustrated and described.

* * * * *

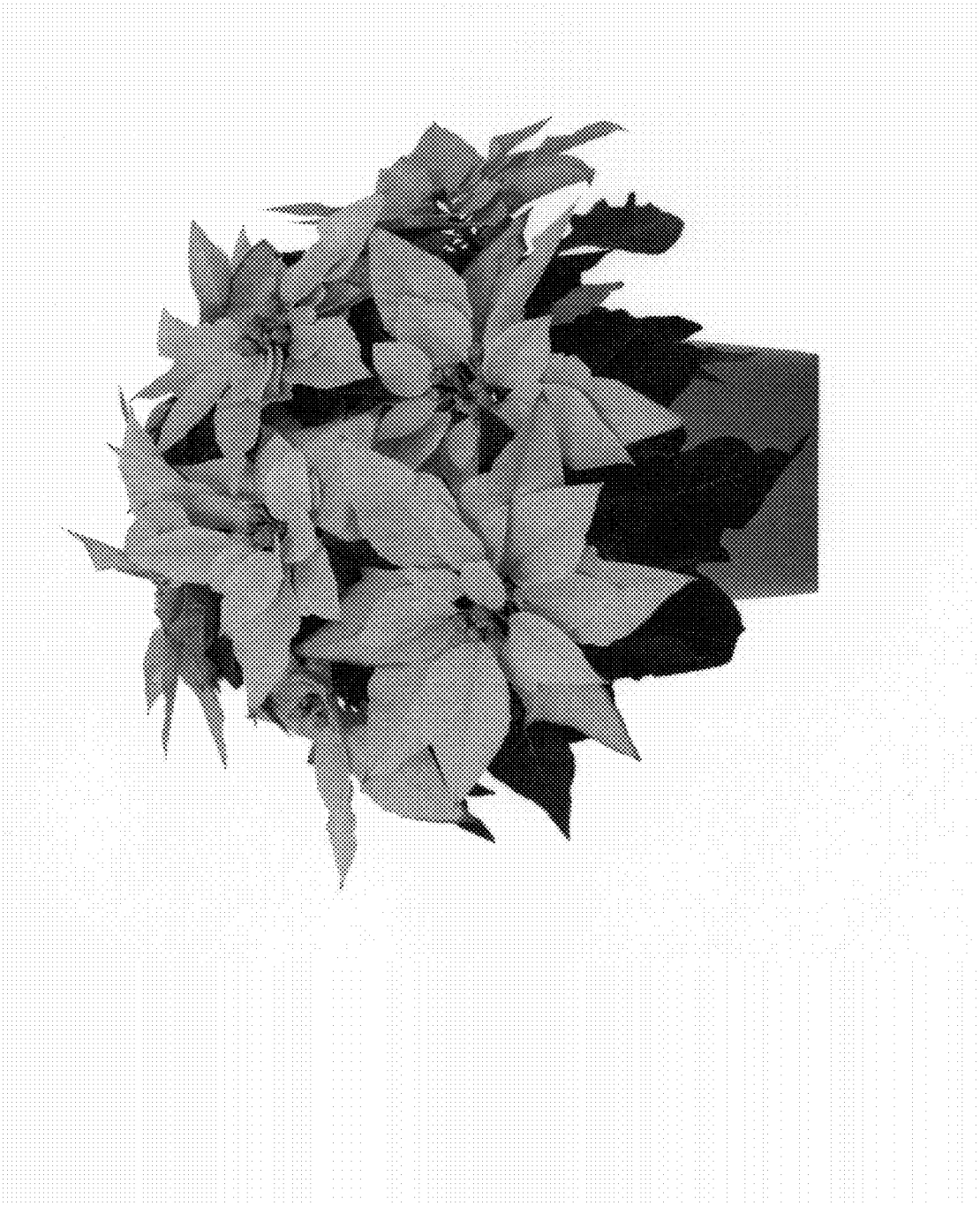

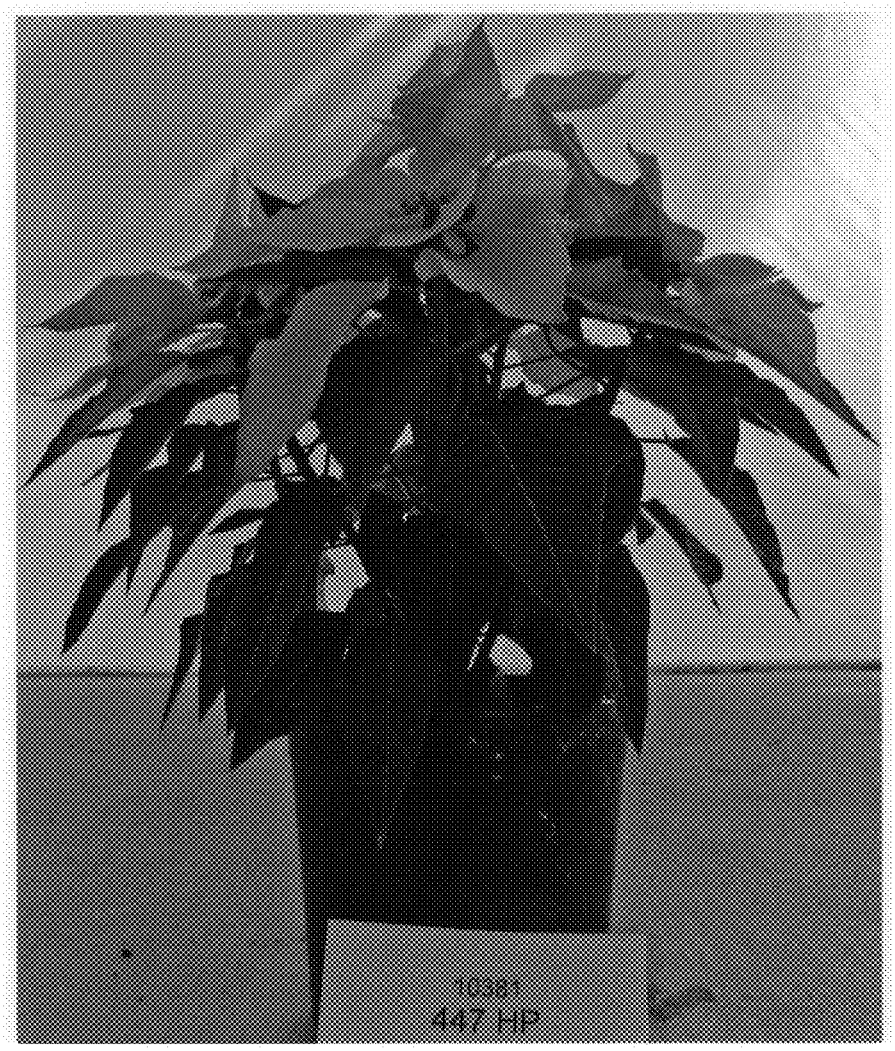
447 HP